United States Patent
Leek et al.

(10) Patent No.: US 9,575,014 B2
(45) Date of Patent: Feb. 21, 2017

(54) MATERIAL DETERMINATION BY SWEEPING A RANGE OF FREQUENCIES

(71) Applicant: Texas Instruments Incorporated, Dallas, TX (US)

(72) Inventors: Alan H. Leek, Frisco, TX (US); Damian M. Szmulewicz, Addison, TX (US)

(73) Assignee: TEXAS INSTRUMENTS INCORPORATED, Dallas, TX (US)

( * ) Notice: Subject to any disclaimer, the term of this patent is extended or adjusted under 35 U.S.C. 154(b) by 59 days.

(21) Appl. No.: 14/578,760

(22) Filed: Dec. 22, 2014

(65) Prior Publication Data

US 2016/0178537 A1     Jun. 23, 2016

(51) Int. Cl.
| | |
|---|---|
| *G01R 27/26* | (2006.01) |
| *G01N 27/00* | (2006.01) |
| *G01N 22/00* | (2006.01) |
| *G01B 3/02* | (2006.01) |
| *H04B 17/12* | (2015.01) |

(52) U.S. Cl.
CPC .................................... *G01N 22/00* (2013.01)

(58) Field of Classification Search
CPC ............. H01Q 1/24; H04B 17/12; H04B 5/00; G01R 27/26; G01N 27/00; G01N 22/00; G01V 3/02
USPC .. 343/702; 324/630, 658, 637; 345/173–178
See application file for complete search history.

(56) References Cited

U.S. PATENT DOCUMENTS

| | | | | |
|---|---|---|---|---|
| 2007/0194878 A1* | 8/2007 | Touge | ..................... | G01S 7/282 340/5.2 |
| 2010/0066696 A1* | 3/2010 | Yang | ..................... | G06F 1/3231 345/173 |
| 2011/0012793 A1* | 1/2011 | Amm | ....................... | H01Q 1/24 343/702 |
| 2011/0250928 A1* | 10/2011 | Schlub | ................... | H04B 17/00 455/550.1 |
| 2013/0217342 A1* | 8/2013 | Abdul-Gaffoor | .... | H03K 17/955 455/77 |
| 2015/0201385 A1* | 7/2015 | Mercer | ............... | H04B 1/3838 455/452.1 |

* cited by examiner

*Primary Examiner* — Tung X Nguyen
*Assistant Examiner* — Neel Shah
(74) *Attorney, Agent, or Firm* — John R. Pessetto; Charles A. Brill; Frank D. Cimino

(57) ABSTRACT

A material-discerning device is arranged to include an antenna, a proximity sensor, a band pass filter and a processor. The antenna radiates a radio-frequency signal and a material object is located in the field created by the antenna and near the proximity sensor. Change in the amplitude of the radio-frequency signal due to the presence of the material object is detected by the proximity sensor. The change in amplitude of the radio-frequency signal is stored. The frequency of the radio-frequency signal is changed and the process is repeated until a range of frequencies have been swept and stored. After the range of frequencies has been swept and stored, the processor determines the type of material of the material object using the results of the changes in amplitude of the radio-frequency signals.

2 Claims, 3 Drawing Sheets

MATERIAL DETERMINATION BY SWEEPING A RANGE OF FREQUENCIES

BACKGROUND

Material media change the properties of electromagnetic energy transmitted through them. Permittivity and permeability are electrical characteristics of material media. The permittivity of a medium describes how much electric flux is generated per unit charge in that medium. Permeability is the measure of the ability of a material to support the formation of a magnetic field within itself. Because material media have different electrical characteristics (i.e. different permittivity and permeability) with respect to electromagnetic energy, material media can be identified by their response to electromagnetic energy.

DETAILED DESCRIPTION

A material-discerning device is arranged to include an antenna, a proximity sensor, a band pass filter and a processor. The antenna radiates a radio-frequency signal and a material object is located in the field created by the antenna and near the proximity sensor. Change in the amplitude of the radio-frequency signal due to the presence of the material object is detected by the proximity sensor. The change in amplitude of the radio-frequency signal is stored. The frequency of the radio-frequency signal is changed and the process is repeated until a range of frequencies have been swept and stored. After the range of frequencies has been swept and stored, the processor determines the material type of the material object using the results of the changes in amplitude of the radio-frequency signals.

Figure 1:
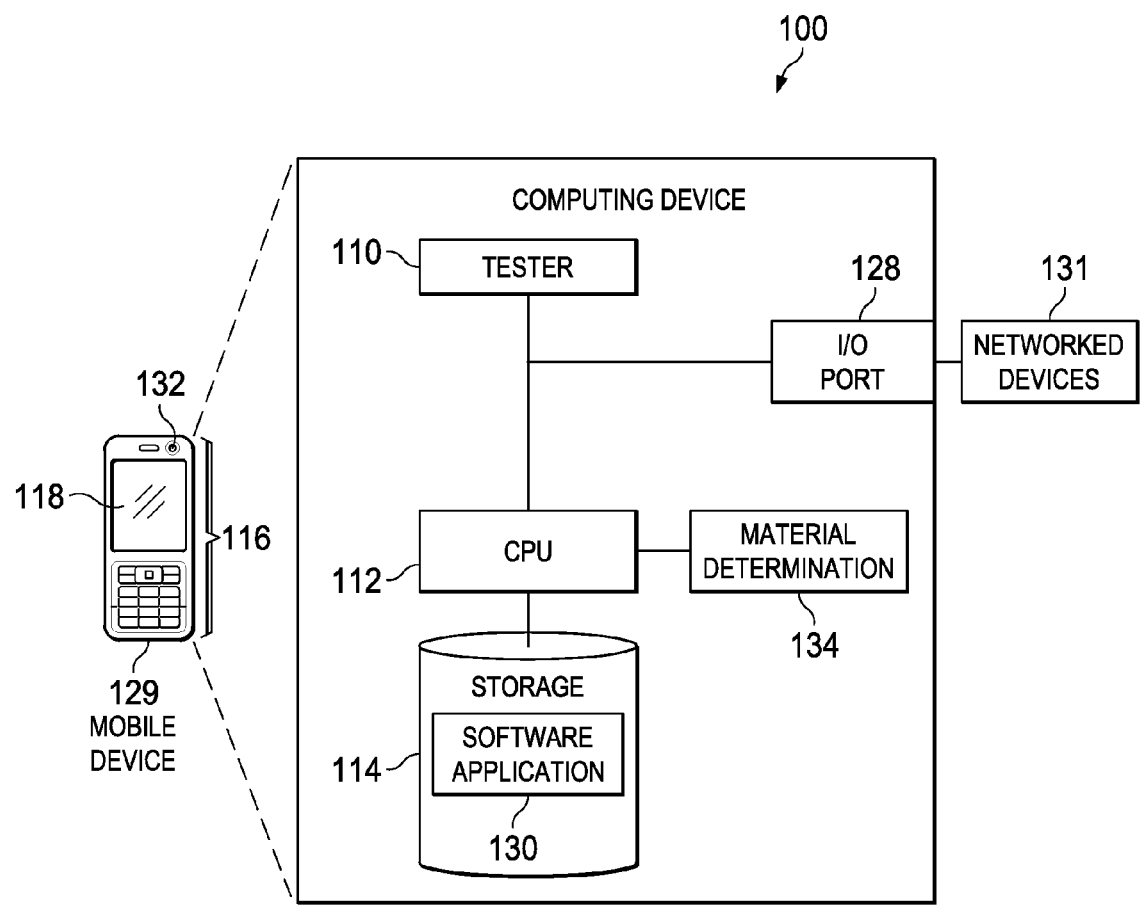
FIG. 1 shows an illustrative computing device in accordance with embodiments of the disclosure.

FIG. 1 shows an illustrative computing device 100 in accordance with embodiments of the disclosure. For example, the computing device 100 is, or is incorporated into, a mobile communication device 129, such as a mobile phone, a personal digital assistant (e.g., a BLACKBERRY® device), a personal computer, automotive electronics, projection (and/or media-playback) unit, or any other type of electronic system.

In some embodiments, the computing device 100 comprises a megacell or a system-on-chip (SoC) which includes control logic such as a CPU 112 (Central Processing Unit), a storage 114 (e.g., random access memory (RAM)) and tester 110. The CPU 112 can be, for example, a CISC-type (Complex Instruction Set Computer) CPU, RISC-type CPU (Reduced Instruction Set Computer), or a digital signal processor (DSP). The storage 114 (which can be memory such as on-processor cache, off-processor cache, RAM, flash memory, or disk storage) stores one or more software applications 130 (e.g., embedded applications) that, when executed by the CPU 112, perform any suitable function associated with the computing device 100. The CPU 112 can include (or be coupled to) a material determination 134 unit, which includes various components arranged in a common (or separate) substrate as disclosed herein below.

The tester 110 is a diagnostic system and comprises logic (embodied at least partially in hardware) that supports monitoring, testing, and debugging of the computing device 100 executing the software application 130. For example, the tester 110 can be used to emulate one or more defective or unavailable components of the computing device 100 to allow verification of how the component(s), were it actually present on the computing device 100, would perform in various situations (e.g., how the components would interact with the software application 130). In this way, the software application 130 can be debugged in an environment which resembles post-production operation.

The CPU 112 comprises memory and logic that store information frequently accessed from the storage 114. The computing device 100 is often controlled by a user using a UI (user interface) 116, which provides output to and receives input from the user during the execution the software application 130. The output is provided using the display 118, indicator lights, a speaker, vibrations, image projector 132, and the like. The input is received using audio and/or video inputs (using, for example, voice or image recognition), and mechanical devices such as keypads, switches, proximity detectors, and the like. The CPU 112 and tester 110 is coupled to I/O (Input-Output) port 128, which provides an interface (that is configured to receive input from (and/or provide output to) peripherals and/or computing devices 131, including tangible media (such as flash memory) and/or cabled or wireless media. These and other input and output devices are selectively coupled to the computing device 100 by external devices using wireless or cabled connections.

As disclosed herein, material-discerning proximity sensing techniques allow an autonomous electronic system to more accurately determine the substance of a proximal object by evaluating characteristics (e.g. permittivity and permeability) of materials that are included by the proximal object.

Figure 2:
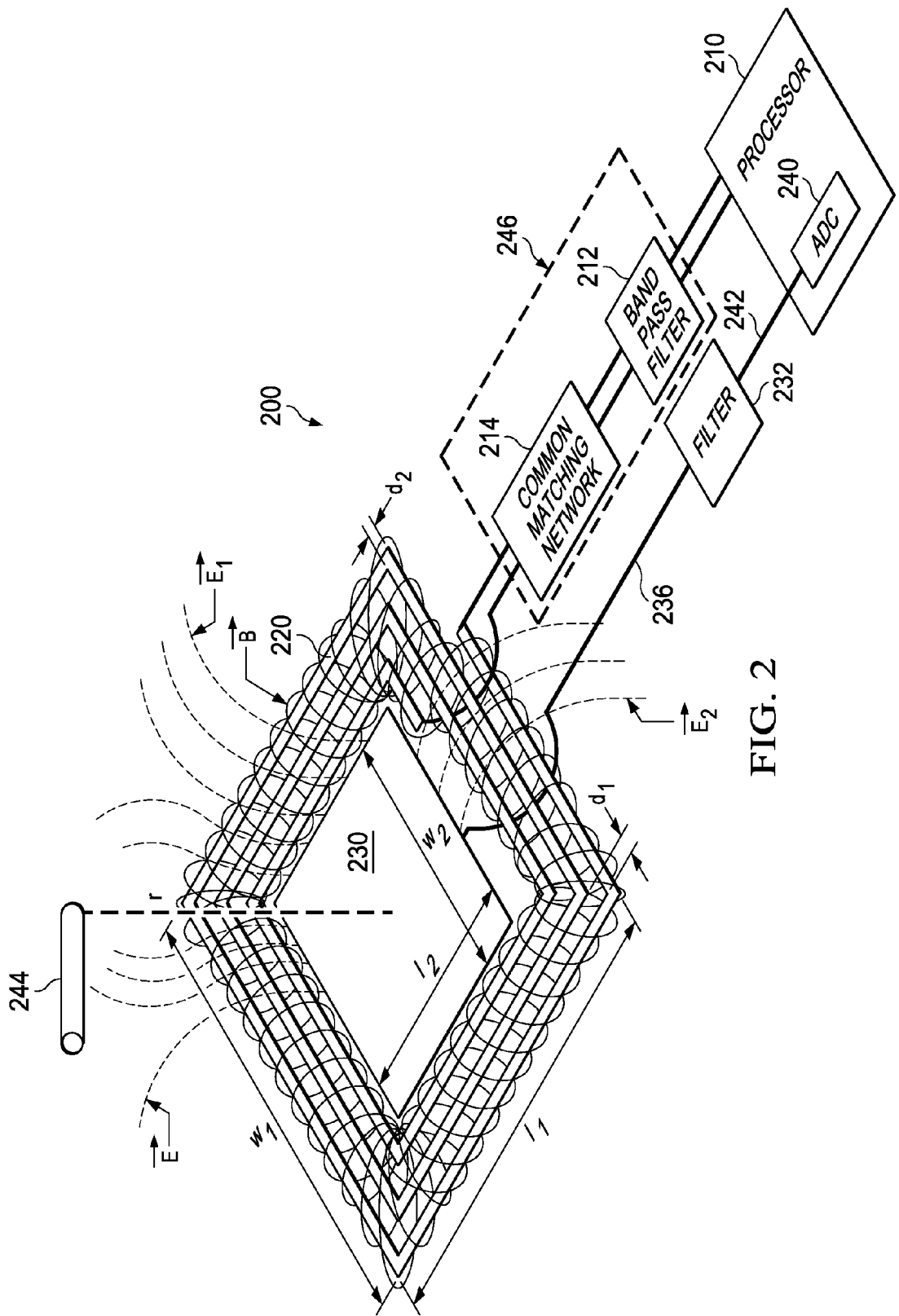
FIG. 2 is a schematic diagram illustrating a material-discerning sensing system in accordance with embodiments of the disclosure.

FIG. 2 is a schematic diagram illustrating a material-discerning in accordance with embodiments of the present disclosure. System 200 is an example autonomous electronic system that is arranged to perform material-discerning sensing. System 200 includes a processor 210, a band pass filter 212, a, common matching network 214, an antenna 220, a proximity sensor 230, a filter 232 and an analog to digital (ADC) converter 240.

Processor 210 is a processor such as CPU 112 that is generally arranged to control functions of system 200 in response to the closeness of the material characteristics of proximal object, such as a metal rod 244. Processor 210 generates and/or controls a single- or dual-ended radio-frequency signal that is adapted to drive antenna 220. The radio-frequency signal is a repetitive wave function, which can be a sine wave, a square wave, or other waveforms suitable for driving antenna 220. For example, a square wave signal can be filtered by band pass filter 212 to pass a fundamental frequency (at a frequency such as 13.56 megahertz). Common matching network 214 is arranged to balance the impedance of the feed lines to the antenna 220 with the characteristic impedance of the antenna 220.

In the illustrated embodiment, antenna 220 is arranged as a coil wherein the antenna, when energized, has an electrical core that extends through a portion of the surface of the proximity sensor 230. The coil of antenna 220 can be arranged as, for example, a series of conductive traces that progressively wind or loop (one or more times) around an inner portion of the proximity sensor 230. When the conductive traces are arranged in a rectilinear fashion, each segment (or group of segments) is shorter (or longer, depending on a direction in which the segments are traversed) such that the segments progressively "spiral" inwards to (or outwards from, depending on the direction in which the segments are traversed) the proximity sensor 230. (In an alternate embodiment, the conductive traces can also be arranged using curved traces to form a curved spiral that is wound around the proximity sensor 230.)

The conductive traces have a length "$l_1$" that is longer than the length "$l_2$" of the proximity sensor 230 and a width "$w_1$" that is wider than the width "$w_2$" of the proximity sensor 230. Each segment of the conductive traces is separated (e.g., by a dielectric) from an adjacent segment of the conductive traces by a distance "$d_1$" and has a width of "$d_0$." Thus the conductive traces are arranged to be mutually inductive and form an electrical field in response to an applied (e.g., time invariant) radio-frequency signal (coupled from the processor 210, for example) being coupled to opposite end of the conductive traces. The conductive traces need not lie in the same plane as the proximity sensor 230, need not surround the capacitive sensor, and even have various shapes, but are arranged to electrically interact with the proximity sensor 230.

The total length of the conductive traces (as well as the number of "turns," the separation between adjacent segments, and width and length of each of the segments) can be selected in accordance with a fraction of the wavelength of the radio-frequency signal (e.g., tone and/or carrier wave) coupled to the antenna 220. The range "r" and directionality of the radiated electric field are also affected by the shape, proportions, trace width, distance between traces, total inner perimeter of the conductive traces and total outer perimeter of the conductive traces.

The electric field is illustrated using field lines $\vec{E}$, where field lines $\vec{E1}$ are generated in association with a capacitive sensor mode and field lines $\vec{E2}$ are generated in association with a radio frequency/material discernment mode. The field lines $\vec{E1}$ illustrate the electric field coupled between the object (to be detected) and the associated portions of the proximity sensor 230 and $\vec{E2}$ illustrate the electric field coupled between coil of antenna 220 and the associated portions of the proximity sensor 230. An upper and lower main lobe of the electric and magnetic fields can be used to detect the object (to be detected) having range "r." The electric field is also associated with magnetic components $\vec{E}$. Both conductive and non-conductive objects can possibly impact the strength of the $\vec{E}$ field of the coil antenna, which is associated with field lines $\vec{E2}$. Thus, in the material discernment mode, as the $\vec{E}$ field is impacted, the $\vec{E2}$ field is thus also impacted, which causes a change in the amplitude on the associated portions of the proximity sensor 230 (due to the changes in the $\vec{E2}$ field), for example.

Thus, the antenna 220 is arranged as a coil that, when energized, generates an electrical field having upper lobes and lower lobes, with a main upper lobe and main lower lobe defining an axis that extends through a portion of the surface of the proximity sensor 230 (as discussed below with respect to FIG. 3). When viewed as an orthogonal projection using an axis of projection (as viewed from above, for example) that is not parallel to a portion of the surface of the proximity sensor 230, the traces appear to surround the proximity sensor 230.

For ease of commercialization, the antenna that is arranged to radiate a radio-frequency signal can be driven using a transmit output power below the FCC threshold requiring certification (e.g., for a frequency band that includes the frequency of the radio-frequency signal coupled to the antenna 220).

Proximity sensor 230 is, for example, a copper fill pad having an area determined as the (multiplication) product of the length "$l_2$" and the width "$w_2$" of the proximity sensor 230. (The aspect ratio of a, for example, rectangular proximity sensor 230 can vary and the area thereof, for example, can be larger or smaller than the area of a human finger.) The copper fill pad of proximity sensor 230 is formed on a fixed substrate such as a printed circuit board (PCB) or formed on a flexible substrate such as a flexible PCB. As discussed above, in an embodiment coil antenna is arranged around the perimeter of the proximity sensor 230.

The proximity sensor 230 is used as a sensor for the discernment of the material of the proximal object by sensing the disruption (and the degree of disruption) of the electric field and magnetic field produced by antenna 220. System 200 uses the proximity pad in conjunction with an electrical quantity sensor such as an ADC (analog-to-digital converter) to measure the level at the applied frequency of the electrical field coupled to the proximity sensor 230 from the surrounding coil antenna 220. As various objects move into the field of the antenna, they impact and interfere with the tuning and efficiency of the antenna 220 and the common matching network 214 (which can be matched to the antenna 220). Objects in the field that are conductive affect characteristics of the magnetic field (and the concomitant electric field) output by the antenna 220 to a substantially greater degree than non-conductive objects. One characteristic of the characteristics of the electric field that is changed is manifested as a change in amplitude of the radio-frequency signal used to generate the electric and magnetic fields coupled to the proximity sensor 230.

The change in amplitude of radio-frequency signal 236 can be detected by using measurements performed by the ADC 240. The ADC 240 forwards the measurements as data to be used by software and/or firmware of the processor 210. The filter 232 is optionally employed to filter the received radio-frequency signal 236 to prevent and/or reduce aliasing of the sampled radio-frequency signal by the ADC 240.

In an embodiment, a low-speed ADC 240 is used to minimize power consumption, complexity, and layout area. With the low-speed ADC 240, under-sampling and aliasing are intentionally used in a manner that allows for signal energy at the ADC 240 input to be detected while providing increased immunity to noise.

Without external filtering (to maintain a low cost, for example), the amplitude of the received radio signal frequency 236 can still be measured by the ADC 240 regardless of degree of aliasing caused by under-sampling (even given a large disparity in sampling rate and Nyquist rates with regards to the frequency of the radio-frequency signal). The proximity sensor 230 that is under-sampled by the ADC 240 thus effectively operates using a broadband input.

The total energy determined by the under-sampled ADC 240 input 242 is determined by, for example, summing the magnitude of the samples over a selected time period (e.g., a tenth of a second). (In an alternate embodiment, a software envelope detector can be arranged to determine the total energy.)

The amplitude of the sampled signal (even without the intervening presence of filter 232) is not substantially incorrectly measured by the ADC 240 when under-sampling the proximity sensor 230. The ADC 240 is able to substantially correctly measure the energy coupled to the proximity sensor 230 because the presence of a proximal conductive object (within range of the electric field) both lowers the energy (signal amplitude as determined by accumulating samples over a selected time period) at the input of the ADC 240, and also tends to shield the system 200 from external noise sources. Accordingly, under-sampling by the ADC 240 provides for increased noise immunity for the system, while also allowing the use of a relatively simple (e.g., low cost) broadband ADC 240 to measure the proximity sensor 230.

In other embodiments, more complex ADCs, comparators, sample and hold circuits, or other common peripherals or other various types of voltage sensors may be used to detect a change in amplitude of radio-frequency signal coupled to proximity sensor 230. The detected change in amplitude of radio-frequency signal 236 coupled to proximity sensor 230 can be detected by accumulating samples over a selected time period using an electrical quantity sensor.

Figure 3:
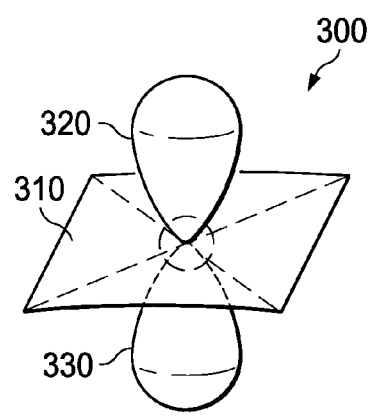
FIG. 3 is a schematic diagram illustrating radiated lobes of a material-discerning sensing sensor in accordance with embodiments of the disclosure.

FIG. 3 is a schematic diagram illustrating radiated lobes of a material-discerning proximity sensing sensor in accordance with embodiments of the disclosure. As shown in FIG. 2, antenna 220 is arranged as a coil that, when energized, generates an electrical field in response to a radio-frequency signal being coupled the antenna 220. In FIG. 3, the electric field 300 is illustrated as a main "lobe" of the generated having an upper lobe 320 and a lower lobe 330, the upper lobe 320 and lower lobe 330 defining an axis that extends through a portion of the surface of the (flexible) capacitive sensor 310. The upper lobe 320 and the lower lobe 330 are illustrated as geometric shapes for the sake of simplicity. In various embodiments the shape of the electric field varies in accordance with the various shapes and arrangements of the antenna 220 and the capacitive sensor 310.

Different materials will present a range of associated permittivity and permeability. The permittivity and permeability can be frequency dependent. Because the permittivity and permeability of materials varies with frequency, the type of material may be identified by measuring the response of materials to a range of transmitted RF frequencies. Frequency ranges, for example, maybe those used by ISM (industrial, scientific and medical) equipment. For example, ISM equipment can use frequency ranges as follows:

| | |
|---|---|
| 6.78 MHz | ±15.0 kHz |
| 13.56 MHz | ±7.0 kHz |
| 27.12 MHz | ±163.0 kHz |
| 40.68 MHz | ±20.0 kHz |
| 915 MHz | ±13.0 MHz |
| 2,450 MHz | ±50.0 MHz |
| 5,800 MHz | ±75.0 MHz |
| 24,125 MHz | ±125.0 MHz |
| 61.25 GHz | ±250.0 MHz |
| 122.50 GHz | ±500.0 MHz |
| 245.00 GHz | ±1.0 GH |

The response to a radio-frequency signal that is driven from antenna 220 in a field that contains a metal rod 244 is received by the proximity sensor 230. The energy coupled to the proximity sensor 230 is manifested as a change in amplitude of the radio-frequency signal used to generate the electric and magnetic fields coupled to the proximity sensor 230. The change in amplitude of radio-frequency signal 236 can be detected by using measurements performed by the ADC 240. The ADC 240 forwards the measurements as data to be used by software and/or firmware of the processor 210. Measuring the change in amplitude of the radio-frequency signal 236 through a range of RF frequencies provides information that can be used to determine the type of material.

A single antenna 220 and front-end 246 may be used, but multiple front-ends and antennas, may be also be used. The use of multiple front-ends and antennas may be dependent on available resources of the processor 210.

The range of the radio-frequency signals 236 includes gross changes in frequency, for example at integer multiples or even at orders of magnitude in difference. The range of the radio-frequency signal 236 can also include slight changes in frequency at each gross step, each of those steps being only a fractional shift of the range of the radio-frequency signal 236. The gross changes are intended to provide the signature of permeability and permittivity dependency of material over a broader range of frequency, while the minor changes in frequency at each step may be required to evaluate the actual magnitude of change in hardware at each gross frequency step (for example, an evaluation of level of impact to the efficiency, matching and coupling of the front-end at each gross frequency step).

After making measurement at many frequencies in the range of the radio-frequency signals 236, the processor will disable generation of the radio-frequency signal 236, and then begin stepping sequentially through the data taken from each frequency in the range of the radio-frequency signals 236. For each frequency in the range of the radio-frequency signals 236, the processor will evaluate in software (with possible hardware facilitation or acceleration), the reading to determine the effective amplitude of the frequency read, as well as other possible characteristics of the reading (for example, other measurements or statistics, including evaluation of noise level, needed for effective processing). This can be achieved by applying a software envelope detector over the data in a given buffer, which can be accomplished by searching for the maximum and minimum values in the buffer and then taking the difference of those two measurements. The processor will save these results from each buffer and then begin evaluating how these amplitudes compare to the other readings taken during the present as well as previous frequency sequence steps. For a given object of given material composition that comes into range of the antenna 220 and the proximity sensor 230, the frequency dependent permittivity and permeability of that object will impact the efficiency, matching and level of coupling of the front-end 246 and antenna 220 uniquely at each output frequency step.

In a simplified implementation, this can be accomplished by simply comparing the relative software envelope detection amplitude readings from each buffer and then mapping that envelope/signature to a predetermined table of materials to be detected. The mapping process can include making a determination of level of difference between each result and the predetermined levels at each frequency. Absolute thresholds can be set for this, but this may also be taken as ratio-metric changes or by other mathematical evaluation.

Figure 4:
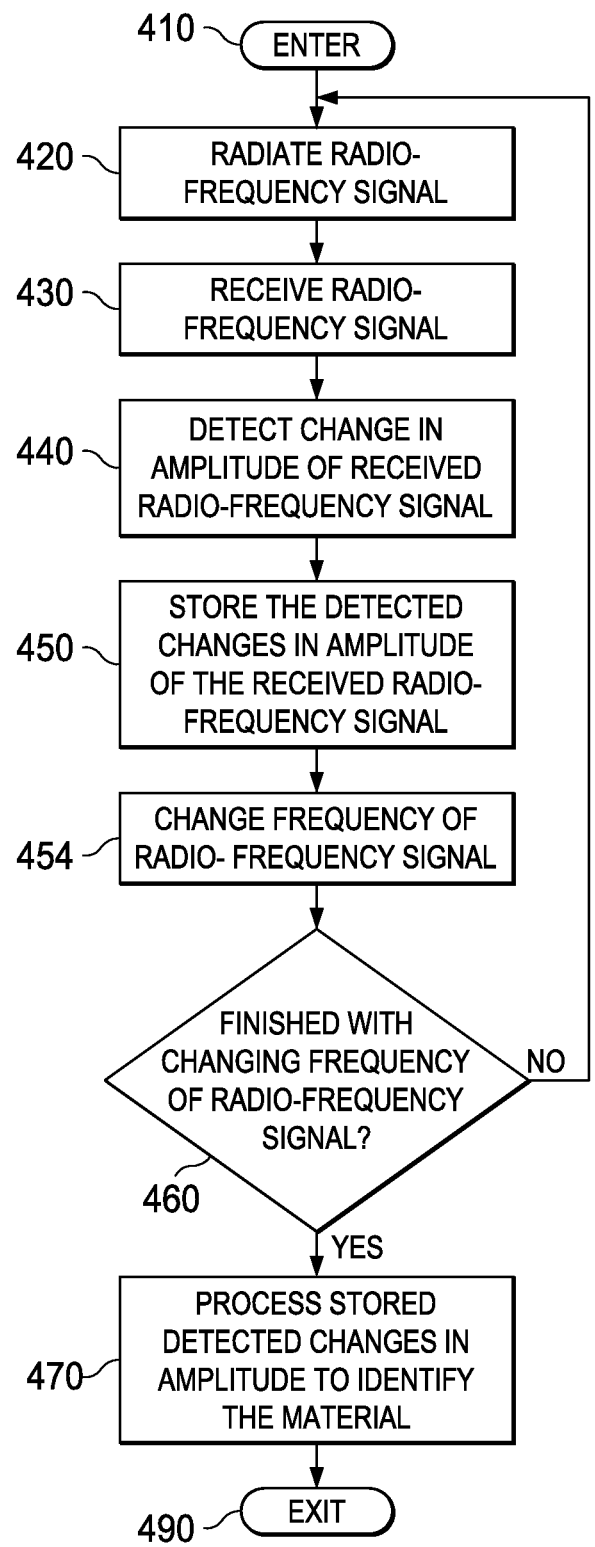
FIG. 4 is a flow diagram illustrating material-discerning sensing in accordance with embodiments of the disclosure.

FIG. 4 is a flow diagram illustrating material-discerning sensing in accordance with embodiments of the disclosure. The program flow illustrated herein is exemplary, and thus various operations within the program flow can be performed in an order that is not necessarily the same as the program flow illustrated herein In operation 420, a radio-frequency signal 236 is radiated by an antenna 220 that is substantially arranged around the proximity sensor 230. Program flow proceeds to operation 430.

In operation 430, the proximity sensor 230 receives the radio-frequency signal 236. A baseline measurement (such as when there is no object in the proximity of the proximity sensor) of the magnitude of the radio-frequency signal 236 can be stored as a baseline measurement. The baseline measurement can be made by under-sampling (e.g., below Nyquist rates) the radio-frequency 236 signal using an ADC as described above to detect an energy level of the first radio-frequency signal received over a selected time period. The under-sampling also increases the relative amount of noise immunity of the system used to perform the material-discerning proximity sensing. The noise is typically generated externally to the system, although noise generated by the system is also possible. Program flow proceeds to operation 440.

In operation 440, a change in the radio-frequency signal 236 is detected. The change in the radio-frequency signal 236 is detected by measuring the magnitude of the radio-frequency signal (using the under-sampling ADC, for example). Program flow proceeds to operation 450.

In operation 450, the detected change in magnitude of the radio-frequency signal 236 is stored. The detected change in magnitude of the radio-frequency signal 236 will later be compared to detected changes in magnitude of the radio-frequency signal across a range of frequencies. Program flow proceeds to operation 454.

In operation 454, the frequency of the radio-frequency signal 236 is changed. The change in the radio-frequency signal 238 is detected by measuring the magnitude of the radio-frequency signal 238 (using the under-sampling ADC, for example). Program flow proceeds to operation 460.

In operation 460, a determination is made as to whether the desired frequency range has been swept. If the desired frequency range has been swept, the program flow proceeds to operation 470. If the desired frequency range has not been swept, the program flow proceeds to operation 420.

In operation 470, the changes in amplitude of the radio-frequency signal 238 as a function of frequency are compared and the material is identified. Program flow proceeds to node 490 and terminates.

The various embodiments described above are provided by way of illustration only and should not be construed to limit the claims attached hereto. Those skilled in the art will readily recognize various modifications and changes that could be made without following the example embodiments and applications illustrated and described herein, and without departing from the true spirit and scope of the following claims.

What is claimed is:

1. A material-discerning device comprising:
   an antenna that is arranged to radiate a radio-frequency signal;
   a proximity sensor that is arranged to detect a change in amplitude of the radio-frequency signal when a material object is located near the antenna and the proximity sensor; and
   a processor that compares the detected change of the radio-frequency signal with a predetermined table of materials;
   wherein the processors determines which material from the predetermined table of materials the material object is composed;
   wherein the processor comprises an analog-to-digital converter, the analog-to-digital converter arranged to quantify the detected change in amplitude of the radio-frequency signal using a sampling rate that is less-than-or-equal-to at least twice the frequency of a carrier wave of the transmitted radio-frequency signal.

2. A method for discerning material comprising:
   radiating a radio-frequency signal using an antenna,
   receiving the radio-frequency signal using a proximity sensor; wherein a material object is located near the antenna and the proximity sensor;
   detecting a change in amplitude of the radio-frequency signal on the proximity sensor;
   storing the detected change of the radio-frequency signal;
   repeating the above steps until a range of frequencies have been radiated; and
   determining the material type of the material object in response to the detected changes in amplitude of the radio-frequency signals;
   using an analog-to-digital converter to quantify detected changes in amplitude of the received radio-frequency signal using a sampling rate that is less-than-or-equal-to at least twice the frequency of a carrier wave of the transmitted radio-frequency signal.

* * * * *